United States Patent [19]

Mancini et al.

[11] Patent Number: 4,537,202
[45] Date of Patent: Aug. 27, 1985

[54] DEVICE FOR DISPLAYING ELECTRICAL SIGNALS OF THE PERIODIC AND/OR SYNCHRONIZABLE TYPE

[75] Inventors: Paolo Mancini, Pisa; Alessandro Taddei, Uzzano; Alberto Macerata; Carlo Marchesi, both of Pisa, all of Italy

[73] Assignee: Remco Italia S.p.A., Milano, Italy

[21] Appl. No.: 412,576

[22] Filed: Aug. 30, 1982

[30] Foreign Application Priority Data

Sep. 2, 1981 [IT] Italy .............................. 68161 A/81

[51] Int. Cl.³ .............................................. A61B 5/04
[52] U.S. Cl. .................................................. 128/712
[58] Field of Search ............... 128/695, 696, 710, 699, 128/711, 712, 660, 661, 731

[56] References Cited

U.S. PATENT DOCUMENTS

| 4,098,267 | 7/1978 | Stein et al. | 128/712 |
| 4,119,090 | 10/1978 | Dehnert | 128/712 |
| 4,340,065 | 7/1982 | Gessman | 128/712 |
| 4,414,981 | 11/1983 | Wong et al. | 128/712 |

FOREIGN PATENT DOCUMENTS 23862  2/1981  European Pat. Off. ............ 128/712

OTHER PUBLICATIONS

Sur et al., "Journal of the Institution of Electronics and Telecommunication Engineers", vol. 22, No. 12, Dec. 1976, pp. 786-790.
Ruiz et al., "Proceedings of an International Symposium" Toulouse, Mar. 22-25, 1977, in Medical Computing.

Primary Examiner—William E. Kamm
Attorney, Agent, or Firm—Jeffers, Irish & Hoffman

[57] ABSTRACT

A device for displaying an electrical signal of the periodic and/or synchronizable type.

The main characteristic of this device is that it comprises:
  a memory in which this electrical signal is sequentially memorized;
  a recognition circuit for recognizing a predetermined electrical pattern and which emits a synchronization signal whenever the electrical signal to be displayed corresponds to the predetermined electrical pattern;
  microprocessor means which correlates the synchronization signal with the electrical signal to be displayed and memorized in the memory in such a way as to identify in the memory a plurality of cycles of the signal to be displayed;
  a cathode ray tube having a screen on which the various cycles of the memorized signal can be displayed; and
  processor means which convert the memorized signal into horizontal (x) and vertical (y) deflection signals of the cathode ray tube, the processor means being operable to derive, for each cycle of the memorized signal corresponding values of the deflection signals in such a way as to generate on the screen of the cathode ray tube a juxtaposed and perspective representation of the wave forms of the cycles of the signal to be displayed.

16 Claims, 5 Drawing Figures a)

b) $x(t, tq(i)) = H1 \dfrac{TO - tq(i)}{LH - tq(i)} + (t - tq(i)) \dfrac{LH - TO}{LH - tq(i)}$ c) $y(t, tq(i)) = H2 \dfrac{TO - tq(i)}{LH - tq(i)} + M(t) \dfrac{LH - TO}{LH - tq(i)}$

DEVICE FOR DISPLAYING ELECTRICAL SIGNALS OF THE PERIODIC AND/OR SYNCHRONIZABLE TYPE

BACKGROUND OF THE INVENTION

The present invention relates to a device for displaying electrical signals of the periodic and/or synchronisable type.

In particular the present invention relates to a display device advantageously usable to effect analysis of electro-cardiographic signals over a long period.

As is known, the long term analysis of electrocardiographic signals is a diagnostic technique used both in coronary treatment units and in dynamic electrocardiography. In the first case it is necessary continuously to supervise the evolution of the electrocardiographic trace of patients at high risk in order to allow a rapid recognition of dangerous electrocardiographic phenomena. In the second case electrocardiographic traces recorded over many hours, even for an entire day, are analysed by means of a unit carried by patients who follow their normal activities; in this way it is possible to identify incidents which, because they manifest themselves in an unpredictable and sporadic manner cannot be detected by conventional electrocardiographic examination.

Given the enormous quantity of information to be interpreted in both the above mentioned cases, instruments have been provided to facilitate the diagonsis by the doctor. In particular, a first group of commercially available instruments perform, in a substantially automatic manner, analyses of electrocardiographic signals, thereby excluding the doctor from the recognition and evaluation of individual incidents. A second group of instruments, also currently commercially available, display the electrocardiographic trace on a monitor, leaving the analysis entirely to the doctor. Systems of the second group have therefore various limitations. First of all they present either only a few electrocardiographic cycles in a sequential and non-synchronised manner, or else a single synchronised electrocardiographic pattern. Given the restricted period of time within which the electrocardiographic pattern appears on the screen, the identification of a possible anomaly is particularly difficult. Even more difficult is the establishment of the correlation between adjacent cardiac cycles; such correlations are in fact very important for identifying the occurrence of slow morphological variations and variations in the rythm.

For the purpose of obviating some of the above-mentioned disadvantages there has also been set up a technique known as "contourograph" on the basis of which adjacent cardiac cycles are recorded in a superimposed and suitably spaced manner on a roll of paper. In this way it is certainly easier to identify the occurrence of the said slow morphological variations and variations in rythm, but it is likewise apparent that a system of this type is entirely impractical when it is desired to analyse traces recorded over more than twentyfour hours because of the time required for the doctor to examine the whole of the electrocardiographic patterns.

SUMMARY OF THE INVENTION

The object of the present invention is that of providing a device for displaying electrical signals, in particular signals of the electrocardiographic type, which will be free from the disadvantages of the known devices of the above mentioned type.

The said object is achieved with the present invention in that it relates to a device for displaying an electrical signal of the periodic and/or synchronisable type, characterised by the fact that it comprises:

- a memory in which the said electrical signal to be displayed is memorised sequentially;
- a recognition circuit for recognising a predetermined electrical pattern and which emits a synchronisation signal whenever the said electrical signal to be displayed corresponds to the said predetermined electrical pattern;
- microprocessor means which correlate the said synchronisation signal with the said electrical signal to be displayed and memorised in the said memory, in such a way as to identify in the said memory a plurality of cycles of the said signal to be displayed;
- a cathode ray tube having a screen on which the various cycles of the signal memorised in the said memory can be displayed; and
- processor means which convert the said signal memorised in the said memory into horizontal and vertical deflection signals of the said cathode ray tube, the said processor means being operable to derive, for each cycle of the said memorised signal, corresponding values of the said deflection signals in such a way as to generate on the screen of the said cathode ray tube a juxtaposed and perspective representation of the wave forms relating to the said cycles of the said signal to be displayed.

BRIEF DESCRIPTION OF THE DRAWINGS

For a better understanding of the present invention a preferred embodiment will now be described, by way of non limitative example, with reference to the attached drawings, in which.

DETAILED DESCRIPTION OF THE INVENTION

Figure 1:
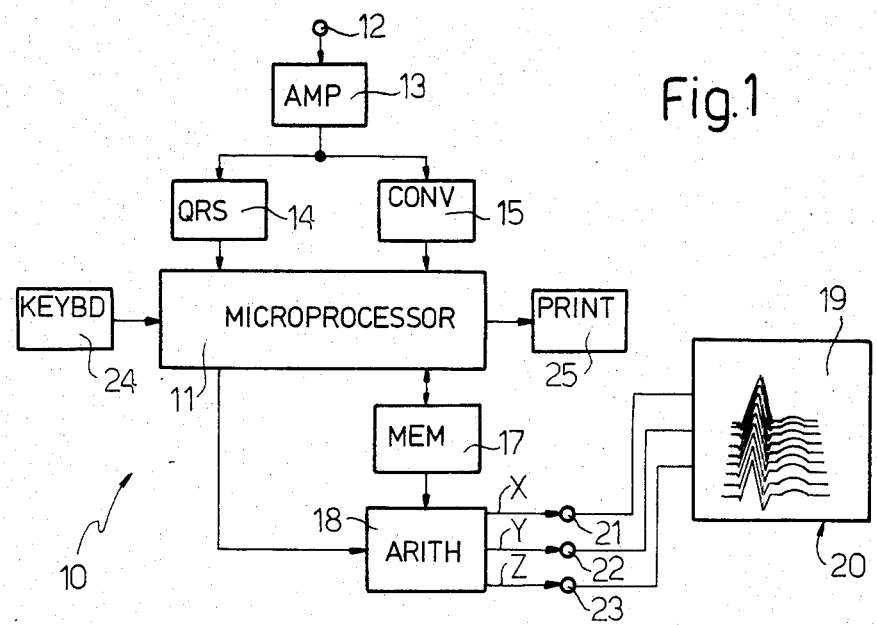
FIG. 1 is a block schematic diagram of a display device formed according to the principles of the present invention.

With particular reference to FIG. 1, a device for displaying electrical signals of the periodic and/or synchronisable type is generally indicated with the reference numeral 10, this device being formed according to the principles of the present invention and being substantially based on a microprocessor unit 11, for example the 8 bit microprocessor of the type 2650 of the firm Signetics having a 4K ROM memory for the resident programme and a 1K RAM for the process variables. The signal to be displayed is supplied to a terminal 12. In the case in which the device 10 is utilised for analysis of the ambulatory type, and in particular for analysis of electrocardiographic traces recorded for many hours by means of a portable unit, the terminal 12 is preferably supplied with the electrical signal at a speed very much greater than the recording speed, for example 32 or 64 times real time. If the device 10 is used for continuously supervising the evolution of the electrocardiographic trace of an in-patient in a coronary treatment unit, the electrocardiographic signal is fed to the terminal 12 in real time.

The terminal 12 is connected to the input of an amplfier 13 the output of which is connected both to a QRS recognition block 14 and to the input of an analogue-to-digital converter 15 in which the electrocardiographic signal is sampled at a predetermined frequency, for example 100 samples per second of real time. The block 14 is substantially of known type and in particular is based on the analysis of the differential of the electrocardiographic signal; this block utilises an algorithm which is implemented in part by hardware and in part by software to satisfy the requirements for the speed of processing in the case in which the analysis of the electrocardiographic trace is effected by means of accelerated reproduction of the trace recorded in real time. The microprocessor unit 11 is connected to a memory 17 in which the signals coming from the analogue-to-digital converter 15 are memorised in sequence. In particular, the unit 11, whenever it receives from the block 14 a signal which indicates the recognition of a QRS pattern, inserts into the memory 17 a code word (QRS mark) in a cell of this memory in which there is contained a sample of the signal which precedes the QRS pattern by several instants. Similarly, the unit 11 inserts into the memory 17 a word with the same code in relation to a QRS (QRSmark) even if it does not receive any signal from the block 14 for an interval of time greater than a predetermined threshold. Conveniently, the memory 17 is constituted by a 16K byte RAM, is static and has an access time of 250 ns. It is used as a circular buffer; in particular, each new sample of a periodic signal is memorised in the position of the oldest sample in such a way that the memory 17 always contains the last 160 seconds of electrocardiographic trace. The memory 17 is likewise connected to an arithmetic unit 18 which also receives signals from the microprocessor unit 11. This arithmetic unit 18 has three outputs respectively connected to terminals 21, 22, 23 which constitute the supply terminals of the axes x,y,z respectively of a deflection system of a cathode ray tube 20. Conveniently the memory 17 is a multiple access type in such a way as to allow both the memorisation of new samples and QRS marks by the microprocessor 11 and the scanning of the memory 17 itself to renew the image on the screen 19 of the cathode ray tube 20 by the arithmetic unit 18. Conveniently the scanning of the memory 17 is effected at a frequency of 800 KHz in such a way as to renew the image on the cathode ray tube at the frame frequency of 50 Hz.

Figure 2:
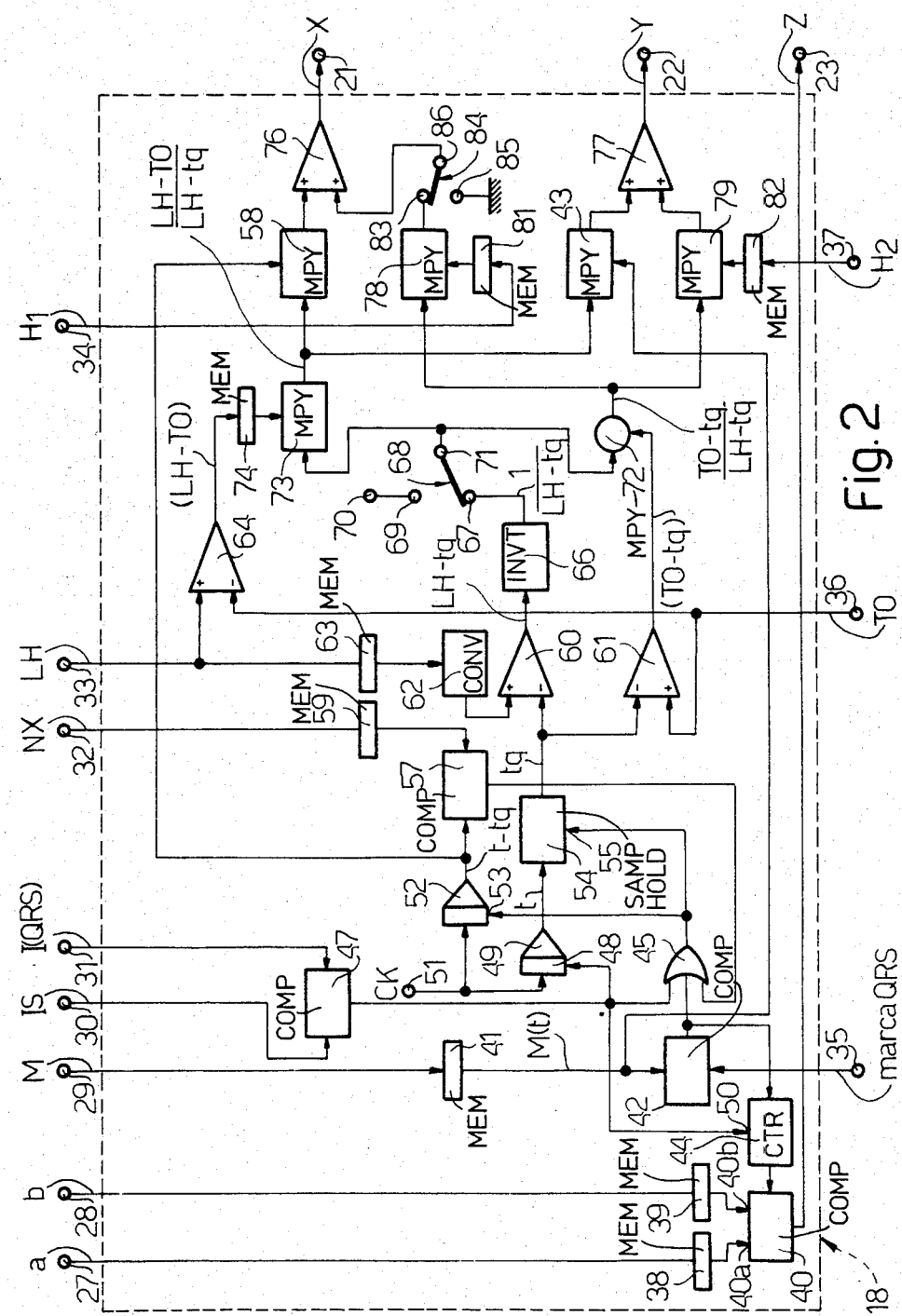
FIG. 2 is a detailed block diagram of the arithmetic unit of FIG. 1.

According to the present invention the arithmetic unit 18, which is illustrated in detail in FIG. 2, converts the signals relating to each sample memorised in the memory 17 into a corresponding pair of x,y signals each of which controls the deflection system of the cathode ray tube 20 in such a way as to represent the various cardiac cycles in a compact manner, superimposed and synchronised over the QRS pattern and with a continuous updating of the image inasmuch as each new cycle is inserted into the lower part of the screen 19 making the oldest pattern move upwards simultaneously. These characteristics are better apparent from the following with reference to FIG. 2 in relation to the structure of the arithmetic unit 18 which allows, according to the present invention, the provision of a perspective representation with variable vanishing points of the whole of the various cardiac cycles memorised in the memory 17.

The microprocessor unit 11 is likewise linked to a programming keyboard 24 and to a printout unit 25 the operations of which are described below.

With particular reference to FIG. 2, the arithmetic unit 18 is supplied with a plurality of electrical signals on connection terminals which are connected in a manner not illustrated to the microprocessor unit 11 or to the memory 17 and which are indicated, in order, with the numerals 27,28, 29, 30, 31, 32, 33, 34, 35, 36, 37. Alongside each terminal there is indicated a letter or a word the significance of which is explained below.

In particular, the terminals 27 and 28 receive two multiple electrical signals a,b each of which relates to a number which defines on the screen of the cathode ray tube 20 (see FIG. 4) the ends of a band of cardiac cycles the luminosity of which is greater than that of adjacent cycles. In the following this band will be indicated the intensified band. The values "a" and "b" are imposed by means of the keyboard 24 and are memorised in respective memories 38, 39 the outputs of which are respectively connected to threshold inputs 40a, 40b of a comparator 40 the output of which is connected to the terminal 23.

The terminal 29 is connected in a manner not illustrated to the output of the memory 17 and receives from this latter, in sequence, the signal which is memorised therein and which from time to time relates to a predetermined cardiac cycle. The terminal 29 is connected to a temporary memory 41 the output of which is connected to a first input and of a comparator 42 and to a first input of a multiplier block 43 conveniently formed with a digital-to-analogue converter. To the second input of a comparator 42 is fed a code signal from the terminal 35 related to the said predetermined value (QRS mark) which the microprocessor unit 11 sets in the memory 17 whenever the block 14 detects a QRS pattern. The comparator 42 has, finally, an output which is connected to the input of a counter 44 the output of which is connected to the signal input of the comparator 40; moreover, the output of the comparator 42 is connected to a first input of a logic gate 45 of the three-input OR type.

The terminals 30 and 31 are supplied from the microprocessor 11 with signals respectively relating to the scanning address of the memory 17 and the address of the mark QRS relating to the last cycle reached in the memory 17 itself and respectively indicated IS, I(QRS). The terminals 30, 31 are both connected to the inputs of a comparator 47, which has an output which is connected to a second input of the OR gate 45, to a zeroing input 48 of a ramp generator 49, and to a zeroing input 50 of the counter 44.

A clock signal (CK) present at a terminal 51 is supplied both to the ramp generator 49 and to an input of a ramp generator 52 which has a zeroing input 53 which is connected to the output of the OR gate 45. The output of the ramp generator 49 is connected to the input of a "sample and hold" circuit 54 which has sampling input 55 also connected to the output of the OR gate 45. The output of the ramp generator 52 is connected to a first input of a comparator 57 and to a first input of a multiplier block 58, conveniently formed with a digital-to-analogue convertor. A second input of the comparator 57 is connected to the output of a memory 59 which has its input connected to the terminal 32; in this memory 59 there is stored a signal NX conveniently established by the operator and fed in by means of the keyboard 24 and substantially relating to the maximum time which it is presumed that a cardiac cycle can have. The output of the comparator 57 is finally connected to a third input of the OR gate 45.

The output of the circuit 54 is connected to the inverting input (−) of operational amplifiers 60,61. To a non-inverting input (+) of the amplifier 60 there is connected the output of a digital-to-analogue convertor 62 to the input of which there is supplied a signal coming from a memory 63 connected to the terminal 33. To the terminal 33 there is supplied, by means of the microprocessor unit 11, a signal proportional to a value LH constituting one of the coordinates of a point of view F (see FIG. 3a) with respect to which the perspective signal on the screen 19 of a cathode ray tube 20 must be constructed. The terminal 33 is likewise connected to the non-inverting input (+) of an operational amplifier 64 which has an inverting input (−) connected to the terminal 36 and to the non-inverting input (+) of the operational amplifier 61. To the terminal 36 there is supplied the signal indicated TO and corresponding, in FIG. 3a, to the time origin. The output of the operational amplifier 60 is connected, by means of an inverting unit 66, to a sampling terminal 67 of a switch 68 which has a further sampling terminal 69 connected to a terminal 70 in turn connected in a manner not illustrated to a source of DC supply. The switch 68 has a common terminal 71 which is connected, respectively, to a multiplier unit 72 which also receives the output of the operational amplifier 61, and to a first input of a further multiplier unit 73. This latter is conveniently formed with a digital-to-analogue convertor and has a second input which is connected to the output of the amplifier 64 by means of a memory 74. The output of the multiplier unit 73 is connected to a second input of the multiplier unit 58 and to a second input of the multiplier unit 43. The output of the unit 58 is connected to a first non-inverting input (+) of an operational amplifier 76 the output of which is connected to the terminal 21. The output of the multiplier block 43 is connected to a first non-inverting input (+) of an operational amplifier 77 the output of which is connected to the terminal 22.

The output of the multiplier block 72 is connected to a first input of the multiplier units 78,79 conveniently formed by means of convertors of the digital-to-analogue type. To a second input of these units 78,79 there is supplied, respectively, a signal H1, H2 from the terminals 34,37, which signals are memorised in a respective memory 81,82. The output of the multiplier unit 78 is connected to a sampling terminal 83 of a switch 84 which has further sampling terminal 85 connected to earth and a common terminal 86 connected to a seond non-inverting input (+) of the operational amplifier 76. The output of the multiplier unit 79 is on the other hand connected to a second non-inverting input of the operational amplifier 77.

Figure 3:
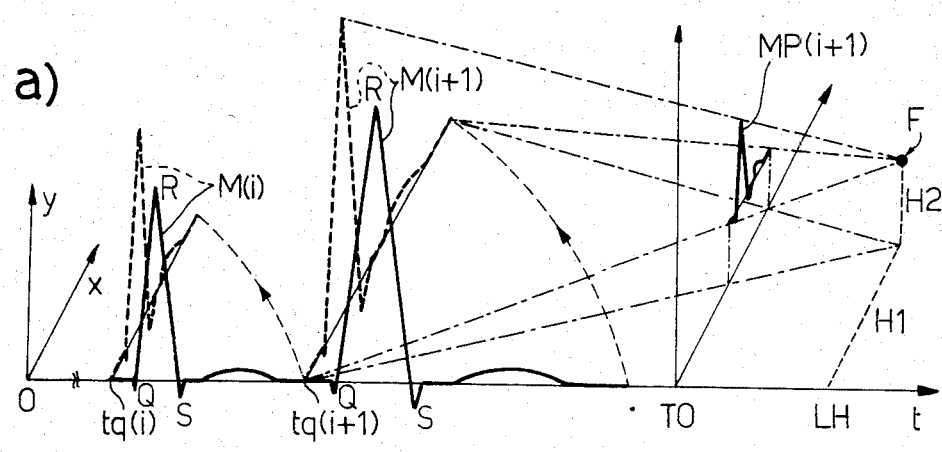
FIG. 3a plots the variation with time of several signals processed by the device in question according to the various formulae set out in FIGS. 3b and 3c.
Figure 4:
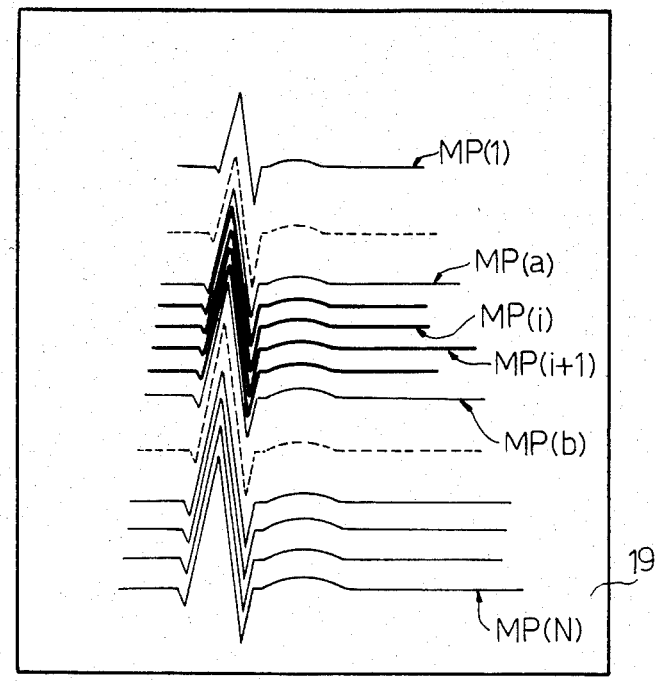
FIG. 4 illustrates an example of how the electrical signals are displayed by means of the subject device.

With particular reference to FIG. 3a, there is shown, as a function of time t, the variation of the electrocardiographic signal supplied to the terminal 12 of FIG. 1. In particular, two complete cycles are illustrated, respectively indicated M(i) and M(i+1) which are consecutive and commence respectively at time t q (i) and at a time t q (i+1); in FIG. 3a there are also shown two axes xy perpendicular to one another and lying in a plane perpendicular to the time axis t; each sample M(i) and M(i+1) is rotated through 90° about the y axis and indicated in broken outline on the plane defined by the xy axes. Moreover, in correspondence with the point on the time axis indicated TO and corresponding to the time origin (which is a point which displaces with real time) there is shown the perspective construction of the sample M(i+1) which, at TO is indicated MP (i+1). In particular, this construction has been made by supposing that the said point of view F has the coordinates LH, H1, H2 as indicated in FIG. 3. In FIGS. 3b and 3c there are shown two formulae which allow the x and y coordinates in the perspective plane for the general sample M(i) to be calculated. It is clear that the value "i" can vary from 1 to N where N is the number of cardiac cycles stored in the memory 17. With particular reference to FIG. 4 there is shown, on an enlarged scale, the screen 19 of the cathode ray tube 20 on which there are shown, in perspective, several of the cycles from 1 to N stored in the memory 17. In particular the cycles contained between the cycles MP(a) and MP(b) are more pronounced in that, as will be seen below, the arithmetic unit 18 has caused an intensification of the signal in relation to the z axis of the cathode ray tube 20 in correspondence with these signals.

Figure 5:
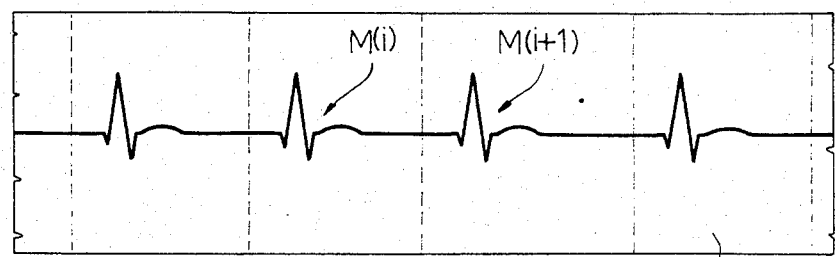
FIG. 5 illustrates an equivalent portion of a trace as it would be recorded on a printing unit.

Finally, with reference to FIG. 5, the cycles lying between MP(a) and MP(b), shown in their real dimensions which are stored in the memory 17, are illustrated as they are traced out to be shown on a sheet 89 produced by the printout unit 25 under the control of the microprocessor unit 11.

The operation of the device 10 is substantially as follows.

With reference to FIG. 1, the electrocardiographic signal is sent to the terminal 12 and, by means of the QRS recognition block 14 and the analogue-to-digial convertor 15 is sent, via the microprocessor unit 11 to the memory 17. In this phase, as already partly explained above, each cardiac cycle identified by a respective QRS pattern is memorised in the memory 17 together with a predetermined value mark which is impressed on a cell of this memory each time that the unit 14 recognises a QRS pattern. The said mark is inserted into the memory 17 even if the block 14 does not recognise a QRS pattern for a time interval greater than a predetermined threshold. Since, as already said, the memory 17 is used as a circular register, each sample which comes from the analogue-to-digital convertor 15 is memorised in the position of the oldest sample in such a way that the memory always contains the information related to the last seconds of the signal, from the terminal 12.

The scanning of the memory 17, conveniently performed at a frequency of 800 KHz, permits the transmission to the arithmetic unit 18 of samples relating to the various memorised cardiac cycles, the address (IS) of the scanning of each cycle, and of address I(QRS) of the last complete QRS received.

With particular reference to FIG. 2, the various samples relating to each cardiac cycle are from time to time transferred into the memory 41. Each of these is compared in the comparator 42 with the signal supplied to the terminal 35 and, when identity of the signals present at the two inputs of the comparator 42 occurs this indicates that in the memory 41 there is contained the information relating to the QRS pattern. In these conditions the comparator 42 emits a signal which increases by one unit the contents of the counter 44 and simultaneously sends a zeroing signal to the input 53 of the ramp generator 52 and an enabling signal to the input 55 of the circuit 54. The instant in which the coincidence between the signals present at the inputs of the comparator 42 takes place identifies, for each cardiac cycle, the commencement instant tq of the cycle itself. At the output of the ramp generator 52 there will therefore be present an electrical signal proportional to the difference between the time t and the instant tq.

When the scanning address (IS) coincides with the address of the last memorised QRS mark I (QRS), the output of the comparator 47 emits a signal which serves to zero the counter 44 and the ramp generators 52 and 49. Since this zeroing takes place in particular only at each complete exploration of the memory 17, a signal present at the output of the ramp generator 49 will be proportional to the time t and will have a saw tooth shape with a period substantially corresponding to the time required to perform a complete scanning of the memory 17. The signal present at the output of the circuit 54 will, on the other hand, be proportional of the time value tq (see FIG. 3a) and will have, overall, a saw tooth form similar to that of the time t but with a waveform which increases stepwise since the sampling is made each time that a signal from the OR gate 45 arrives at the input 55 of this circuit 54.

The OR gate 45 emits an output signal not only for the reasons already mentioned (recognition of a QRS pattern by the comparator 42, conicidence between the scanning address (IS) and the address of the last memorised QRS mark (I QRS)), but also when the output signal from the ramp generator 52 then present at the input of the comparator 57 exceeds the value of the signal (NX) memorised in the memory 59. In particular, the signal NX is set by the microprocessor 11 and corresponds to a maximum time for the cardiac cycle within which a QRS pattern must be found; therefore, if a possible pattern fails to appear beyond this predetermined time it automatically makes the ramp generator 52 start up again by means of the comparator 57 and the OR gate 45.

The signals tq and (t-tq) are then summed, subtracted and multiplied in the part of the arithmetic unit 18 located downstream of the ramp generator 52 and the circuit 54 in such a way as to obtain at the terminals 21,22 the values of x,y as shown in FIGS. 3b and 3c. In particular, the required values of LH, H1 and H2 are provided by the microprocessor 11 to the terminals 33, 34 and 37 respectively and are conveniently programmable by the operator by means of the keyboard 24. In this way the operator can select the vanishing point "F" most suited to display the whole of the cardiac cycles memorised in the memory 17 and this will also be possible by acting on the switches 68 and 84 of FIG. 2 in such a way as to exclude any addenda or factors which appear in the formulae cited in FIGS. 3b and 3c. There is therefore obtained, with reference to FIG. 4, a dynamic type perspective representation of the various cardiac cycles in that each new cycle is inserted into the lower part of the screen 19 making the older cycles slide upwards simultaneously whilst the very oldest cycle (MP1) disappears from the upper part of the screen. The time taken for displacement on the screen 19 depends on the speed of analysis; in particular, this speed will be rather low in the case of continuous surveillance of the evolution of the electrocardiographic trace of a patient at high risk in a coronary treatment unit, whilst it will be rather high (of the order of 32 or 64 times the speed of recording, in the case of analysis of traces recorded over many hours).

As illustrated in FIG. 4, the operator can intensify a group of cardiac cycles represented on the screen 19 by acting on the keyboard 24 in such a way as to set into the memories 38 and 39 of FIG. 2 two numbers (a, b) which identify the ends of the band which it is desired to intensify. In this case, when output signal generated by counter 44 and corresponding to the number of cardiac cycles represented in that instant, lies between the numbers contained in the memory 38 and 39, the output of the comparator 40 emits a signal which is sent via the terminal 23, to the z axis of the cathode ray tube 20. This signal therefore serves to increase the luminous intensity of the ray which strikes the screen 19 for each of the cycles lying between the ends "a" and "b".

If the operator wishes now to print these cycles onto paper (see FIG. 5) it will be sufficient to stop the flow of information supplied to the terminal 12 and, by means of the keyboard 24, to control the printout of information contained in the memory 17 and relating to the cardiac cycles the reference numbers of which lie between the ends "a" and "b" mentioned above.

From an examination of the characteristics of the device 10 formed according to the principles of the present invention it can be seen that it allows the above mentioned objects to be achieved.

In particular, from a study of FIG. 4 it can be observed how this type of representation makes both the morphological details of the cardiac cycles and the variations in rhythm very apparent. This representation moreover renders the variations between adjacent cycles very evident in that these latter are now substantially superimposed so that even small differences are now easily identifiable.

The dynamic behaviour of the device 10, not perceptible in the static representation of FIG. 4, in reality strongly increases the analytical capacity. In fact, the perceptive capacity of the observer is increased by the correspondence which exists between the displacement of the image and the natural temporal evolution of the electrocardiographic signal. The device 10 is advantageously usable both in the long term surveillance of the electrocardiographic signal in patients subjected to ambulatory control, and in continuous surveillance of inpatients in coronary intensive care units. In the first case it is, in fact, possible to analyse the whole trace of even 24 hours in an accurate manner and in a conveniently short time (of the order of about 20 minutes); in the second case the representation over a long period allows both a discontinuous observation of the screen 19 by the supervisory staff, and the corellation of many cardiac cycles over a sufficiently wide context, of the order of 2-3 minutes.

Finally, it is clear that the device 10 can have modifications and variations introduced thereto without by this departing from the scope of the present invention.

In particular, although the device 10 has been described for displaying cardiac cycles, it lends itself also in general to display of any pseudo periodic and/or synchronisable signal, the main characteristics of the invention, that is, substantially, the possibility of regulating the position of the point of view F, the dynamic representation of cycles, as well as the possibility of regulating the speed of representation of the cycles themselves remaining the same.

We claim:

1. A device for displaying periodic synchronisable electrical signals comprising:
   input means for receiving an electrical signal to be displayed;
   first memory means (17) for sequentially memorizing samples of said signal to be displayed;
   recognition means (14) connected to said input means for generating a synchronization signal upon recognizing a correspondence between said signal to be displayed and said predetermined pattern;
   microprocessor means (11) connected to said recognition means (14) and to said first memory means for (17) causing said first memory means (17) to store a predetermined signal and causing a plurality of cycles of the signal to be displayed to be identified in said memory upon receipt of each said synchronization signal;
   processor means (18) connected to said first memory means (17) and to said microprocessor means (11) for generating horizontal and vertical cathode ray tube deflection signals from said memorized samples of said signal to be displayed for each of said identified cycles;
   said processor means (18) including first comparator means (42) for comparing a reference signal with said stored predetermined signal and for generating a cathode ray tube horizontal axis synchronization output signal (x) when said stored predetermined signal is equal to said reference signal;
   said processor means (18) including a horizontal deflection signal generator (52), said output signal of said first comparator (42) connected to a zeroing input of said horizontal deflection signal generator;
   said processor means (18) further including a threshold comparator (57) having input means, a first of said threshold comparator inputs provided by the output of said horizontal deflection generator (52) and a second of said threshold comparator inputs supplied with a signal having an adjustable amplitude, the output of said threshold comparator connected to said zeroing input;
   a cathode ray tube (20) including a screen (19) connected to said processor means;
   whereby a perspective, juxtaposed, representation of the wave form corresponding to said identified cycles is displayed on said screen.

2. A device according to claim 1, wherein said microprocessor means (11) includes means (24) for selecting the values of the coordinates (LH, H1, H2) of the vanishing point of said perspective representation.

3. A device according to claim 1 including an analogue-to-digital convertor (15) connected to said input means (12) and said microprocessor means (11) which for converting the said electrical signal to be displayed into a corresponding plurality of digital samples, each of which is transmitted sequentially to the first memory (17) by the said microprocessor means (11).

4. A device according to claim 3, wherein said first memory (17) comprises a circular register connected to said analogue-to-digital convertor means and wherein each new digital sample generated by the said analogue-to-digital convertor (15) is memorised in the position of the sample contained in the said first memory for the longest time.

5. A device according to claim 1, wherein said predetermined signal (QRS mark) is stored in the said first memory (17) several samples before the signal to be displayed corresponding to the said predetermined pattern.

6. A device according to claim 1, wherein said horizontal deflection generator (52) is a ramp generator.

7. A device according to claim 1, wherein said processor means (18) includes second comparator means (47) to which are supplied, respectively, an electrical signal relating to a scanning address (IS) of the said memory (17) and a signal relating to an address (IQRS) of the last of the said predetermined signals (QRS mark) memorised in the said memory (17), and which emits a synchronisation signal for the vertical deflection axis (Y) of the said cathode ray tube (20) each time that the said signal relating to the scanning address (IS) is equal to the said signal relating to the address (IQRS) of the last memorised said predetermined signal (QRS mark).

8. A device according to claim 7, wherein the output of the said second comparator means (47) is connected to the zeroing input (48) of a vertical deflection signal generator (49) of the said cathode ray tube (20).

9. A device according to claim 8, wherein said vertical deflection generator (49) is a ramp generator.

10. A device according to claim 8, including a sample and hold circuit (54) and a sampling enabling circuit (48) and wherein the output of the said ramp generator (49) is connected to the input of said sample and hold circuit, said samping enabling circuit (48) and said sample and hold circuit (54) respectively connected to the output of the said second comparator means (47) and the output of the said threshold comparator (57).

11. A device according to claim 10, wherein the said processor means (18) includes calculator means for calculating the said deflection signals (x,y), the said calculator means being located downstream of the said generators (49,52) and being connected to second memory means (63,81,82) in which are stored the values of the coordinates (LH,H1,H2) of said perspective representation.

12. A device according to claim 7, including a counter (44) having a signal input connected to the output of the said first comparator means (42), a zeroing input (50) connected to an output of the said second comparator means (47), and an output connected to a first input of a second threshold comparator (40), the said comparator (40) being provided with second (40a) and third (40b) inputs to which are supplied electrical signals of predetermined value respectively defining lower and upper threshold values, and having an output connected to a deflection system terminal of said cathoe ray tube (20) whereby an intensification of the wave form of the signals contained in the said memory is generated each time that the value of the signal present at the said first input of the said comparator (40) lies between the values of the signals present at the said second and third inputs.

13. A device according to claim 12, including third and fourth memory means, for respectively storing said electrical signals defining the said lower and upper thresholds.

14. A device according to claim 1, including a printout unit (25) for printout of the said signal contained in the said first memory (17).

15. A device according to claim 1, wherein said input means is supplied with a signal directly derived from a cardiac activity detector.

16. A device according to claim 1 wherein said input is supplied with a signal taken from a recorder connected to a cardiac activity detector and supplied to the said device at a speed greater than the speed at which it has been recorded.

* * * * *